United States Patent
Rollat et al.

(10) Patent No.: US 6,520,186 B2
(45) Date of Patent: Feb. 18, 2003

(54) RESHAPABLE HAIR STYLING COMPOSITION COMPRISING SILICON-CONTAINING POLYCONDENSATES

(75) Inventors: Isabelle Rollat, Paris (FR); Henri Samain, Bièvres (FR)

(73) Assignee: L'Oreal, Paris (FR)

( * ) Notice: Subject to any disclaimer, the term of this patent is extended or adjusted under 35 U.S.C. 154(b) by 16 days.

(21) Appl. No.: 09/769,311

(22) Filed: Jan. 26, 2001

(65) Prior Publication Data

US 2002/0147268 A1 Oct. 10, 2002

(51) Int. Cl.$^7$ .............................. A45D 7/04; A61M 7/11; B65D 83/14
(52) U.S. Cl. .............. 132/203; 132/202; 132/210; 222/335; 222/394; 222/395; 424/45; 424/70.1; 424/70.12; 424/70.122; 424/70.11; 424/DIG. 1; 524/588; 524/838; 525/452; 525/453; 525/474; 528/28; 528/38; 514/772.1
(58) Field of Search .................... 528/28, 38; 525/452, 525/453, 474; 524/588, 838; 132/202, 203, 210; 514/772.1; 424/45, 70.1, 70.12, 70.122, 70.11, DIG. 1, DIG. 2; 222/335, 394, 395

(56) References Cited

U.S. PATENT DOCUMENTS

| | | | |
|---|---|---|---|
| 3,479,310 A | 11/1969 | Dieterich et al. | |
| 3,941,733 A | 3/1976 | Chang | |
| 3,983,291 A | 9/1976 | Chang | |
| 4,567,228 A | 1/1986 | Gaa et al. | |
| 4,738,992 A | 4/1988 | Larson et al. | |
| 5,041,494 A | 8/1991 | Franke et al. | |
| 5,120,531 A * | 6/1992 | Wells et al. | 424/70.11 |
| 5,120,532 A * | 6/1992 | Wells et al. | 424/70.11 |
| 5,302,385 A | 4/1994 | Khan et al. | |
| 5,554,686 A | 9/1996 | Frisch et al. | |
| 5,616,400 A | 4/1997 | Zhang | |
| 5,643,581 A | 7/1997 | Mougin et al. | |
| 5,650,159 A | 7/1997 | Lion et al. | |
| 5,679,754 A | 10/1997 | Larson et al. | |
| 5,756,633 A | 5/1998 | Larson | |
| 5,879,668 A | 3/1999 | Hanna et al. | |
| 5,919,860 A | 7/1999 | Roesler et al. | |
| 5,952,445 A | 9/1999 | Roesler et al. | |
| 5,968,495 A * | 10/1999 | Bolich et al. | 424/401 |
| 5,972,354 A | 10/1999 | de la Poterie et al. | |
| 5,981,650 A | 11/1999 | Zhao et al. | |
| 5,997,886 A * | 12/1999 | Peffly et al. | 424/401 |
| 6,011,126 A | 1/2000 | Dubief et al. | |
| 6,046,295 A | 4/2000 | Frisch et al. | |
| 6,056,945 A | 5/2000 | Cauwet-Martin et al. | |
| 6,090,376 A | 7/2000 | Dubief et al. | |
| 6,111,010 A | 8/2000 | Yu et al. | |
| 6,165,444 A | 12/2000 | Dubief et al. | |
| 6,166,093 A * | 12/2000 | Mougin et al. | 424/401 |
| 6,319,959 B1 * | 11/2001 | Mougin et al. | 424/401 |
| 2002/0041858 A1 * | 4/2002 | Garnier et al. | 424/70.11 |
| 2002/0059941 A1 * | 5/2002 | Garnier et al. | 132/210 |

FOREIGN PATENT DOCUMENTS

| | | |
|---|---|---|
| EP | 0 636 361 | 2/1995 |
| EP | 0 751 162 | 1/1997 |
| EP | 0 791 351 | 8/1997 |
| EP | 0 937 451 | 8/1999 |
| EP | 0 938 889 | 9/1999 |
| FR | 2743297 | 7/1997 |
| FR | 2788972 | 8/2000 |
| JP | 10-203937 | 8/1998 |
| WO | WO 97/12588 | 4/1997 |
| WO | WO 97/14395 | 4/1997 |
| WO | WO 97/17052 | 5/1997 |
| WO | WO 97/46210 | 12/1997 |
| WO | WO 98/38969 | 9/1998 |
| WO | WO 99/58100 | 11/1999 |
| WO | WO 99/63955 | 12/1999 |
| WO | WO 00/12051 | 3/2000 |
| WO | WO 00/12055 | 3/2000 |
| WO | WO 00/12056 | 3/2000 |
| WO | WO 00/15182 | 3/2000 |
| WO | WO 00/25736 | 5/2000 |

OTHER PUBLICATIONS

Derwent Abstract of EP 0 751 162.
Derwent Abstract of EP 0 791 351.
Derwent Abstract of EP 0 938 889.
Derwent Abstract of FR 2,743,297.
Derwent Abstract of FR 2,788,972.
Derwent Abstract of JP 10–203937.
English language translation of JP 10–203937.
Dialog Abstract of JP 10–203937.
Co–pending U.S. application No. 09/380,467; Attorney Docket No.: 05725.0471–00000 Title: Hairstyling Composition Capable of Being Remodelled Inventors: Isabelle Rollat et al. U.S. Filing Date: Sep. 3, 1999.
Co–Pending U.S. application No. 09/627,121; Attorney Docket No.: 05725.0661–00000 Title: Reshapable Hair Styling Composition Comprising Aqueous Colloidal Dispersions of Sulfonated Polyurethane Urea Inventors: Isabelle Rollat et al. U.S. Filing Date: Jul. 27, 2000.
Co–pending U.S. application No. 09/627,055; Attorney Docket No.: 05725.0662–00000 Title: Reshapable Hair Styling Composition Comprising Acrylic Emulsions Inventors: Isabelle Rollat et al. U.S. Filing Date: Jul. 27, 2000.

(List continued on next page.)

*Primary Examiner*—Robert Dawson
*Assistant Examiner*—Jeffrey B. Robertson
(74) *Attorney, Agent, or Firm*—Finnegan, Henderson, Farabow, Garrett & Dunner, L.L.P.

(57) ABSTRACT

A reshapable hair styling composition comprising at least one silicon-containing polycondensate chosen from polyurethanes, polyureas, and polyurethane-ureas, such as a polycondensate that is functionalized with at least one hydrolyzed or hydrolyzable silyl group, wherein said composition provides a reshapable effect.

87 Claims, No Drawings

OTHER PUBLICATIONS

Co-pending U.S. application No. 09/627,785; Attorney Docket No.: 05725.0663–00000 Title: Reshapable Hair Styling Composition Comprising Polyurethane Dispersions Inventors: Isabelle Rollat et al. U.S. Filing Date: Jul. 27, 2000.

Co-pending U.S. application No. 09/695,392; Attorney Docket No.: 05725.0756–00000 Title: Reshapable Hair Styling Compositions Comprising Acrylic Copolymers Inventors: Isabelle Rollat et al. U.S. Filing Date: Oct. 25, 2000.

Co-pending U.S. application No. 09/866,013; Attorney Docket No.: 05725.0911–00000 Title: Reshapable Hair Styling Composition Comprising Heterogenous (Meth)Acrylic Copolymer Particles Inventors: Isabelle Rollat et al. U.S. Filing Date: Jun. 22, 2001.

Co-pending U.S. application No. 09/866,009; Attorney Docket No.: 05725.0912–00000 Title: Reshapable Hair Styling Composition Comprising (Meth)Acrylic Copolymers of Four or More Monomers Inventors: Isabelle Rollat et al. U.S. Filing Date: Jun. 22, 2001.

Co-pending U.S. application No. 10/023,330; Attorney Docket No.: 05725.0922–00000 Title: Reshapable Hair Styling Rinse Composition Comprising (Meth)Acrylic Copolymers Inventors: Isabelle Rollat et al. U.S. Filing Date: Dec. 20, 2001.

Co-pending U.S. application No. 10/022,253; Attorney Docket No.: 05725.0959–00000 Title: Reshapable Hair Styling Non–Rinse Composition Comprising (Meth)Acrylic Copolymers Inventors: Isabelle Rollat et al. U.S. Filing Date: Dec. 20, 2001.

Bremenson et al., English Abstract of Fr 2782637 A1, Mar. 2000.*

* cited by examiner

RESHAPABLE HAIR STYLING COMPOSITION COMPRISING SILICON-CONTAINING POLYCONDENSATES

The present invention relates to a reshapable hair styling composition.

Fixing the hairstyle is an important element in hair styling, and involves maintaining a shaping that has already been carried out, or simultaneously shaping and fixing the hair.

In accordance with the invention, the term "hair styling composition" relates to any kind of hair composition that can be used to effect hair styling, for example fixing compositions, shampoos, conditioners, permanent waving compositions, hair care products, and hair treatment products.

The most prevalent hair styling compositions on the cosmetic market for shaping and/or maintaining the hairstyle are spray compositions comprising a solution, usually alcohol- or water-based, and one or more materials, generally polymer resins. One of the functions of polymer resins is to form links between the hairs, these materials also being called fixatives, in a mixture with various cosmetic adjuvants. This solution is generally packaged either in an appropriate aerosol container, which is pressurized with the aid of a propellant, or in a pump flask.

Other known hair styling compositions include styling gels and mousses, which are generally applied to the wetted hair before brushing or setting it. In contrast to the conventional aerosol lacquers, these compositions have the disadvantage that they do not allow the hair to be fixed in a shape created before their application. In fact, these compositions are essentially aqueous and their application wets the hair and is therefore unable to maintain the initial shape of the hairstyle. In order to shape and fix the hairstyle, therefore, it is necessary to carry out subsequent brushing and/or drying.

Such hair styling compositions all have the same disadvantage that they do not allow the hairstyle to be later modified to a desired shape, which is other than that formed initially, without starting the styling and fixing operations again. Moreover, under various kinds of stress, the hairstyle has a tendency to take on an undesirable permanent set, which cannot easily be modified. Also in the styling process, one desires hair conditioning benefits, such as ease of combing and soft hair feel appearance.

A subject of the invention is a reshapable hair styling composition comprising at least one silicon-containing polycondensate chosen from polyurethanes, polyureas, and polyurethane-ureas, wherein said composition provides a reshapable effect.

Another subject of the invention is a reshapable hair styling composition comprising at least one silylated polycondensate chosen from polyurethanes, polyureas, and polyurethane-ureas, wherein said composition provides a reshapable effect.

Another subject of the invention is a reshapable hair styling composition comprising at least one siliconated polycondensate chosen from polyurethanes, polyureas, and polyurethane-ureas, wherein said composition provides a reshapable effect.

Another subject of the invention is a reshapable hair styling composition comprising at least one polycondensate that is functionalized with at least one group chosen from hydrolyzed silyl groups and hydrolyzable silyl groups, wherein said at least one polycondensate is the product of reactants comprising:

(a) at least one isocyanate terminated polycondensate prepolymer, which is the product of reactants comprising
  (i) at least one polyisocyanate and
  (ii) at least one polyol;
(b) at least one polyfunctional chain extender;
(c) at least one silyl containing component; and
(d) at least one hydrophilic component, wherein said composition provides a reshapable effect.

Another subject of the invention is a reshapable hair styling composition comprising at least one silicon-containing polycondensate chosen from polyurethanes, polyureas, and polyurethane-ureas, such as a silylated polycondensate, a siliconated polycondensate, or a polycondensate that is functionalized with at least one group chosen from hydrolyzed silyl groups and hydrolyzable silyl groups, as described above, wherein said reshapable hair styling composition is in the form of a spray, aerosol, mousse, gel, stick, mud, or lotion.

Another subject of the invention is an aerosol device comprising a vessel, which comprises: (1) an aerosol composition, which provides a reshapable effect and comprises a liquid phase comprising at least one composition comprising at least one silicon-containing polycondensate chosen from polyurethanes, polyureas, and polyurethane-ureas, such as a silylated polycondensate, a siliconated polycondensate, or a polycondensate that is functionalized with at least one group chosen from hydrolyzed silyl groups and hydrolyzable silyl groups, as described above, and a propellant, and (2) a dispenser.

Another subject of the invention is a method of cosmetically treating hair, comprising applying to the hair before, during, or after shaping of a hairstyle of said hair a composition comprising at least one silicon-containing polycondensate chosen from polyurethanes, polyureas, and polyurethane-ureas, such as a silylated polycondensate, a siliconated polycondensate, or a polycondensate that is functionalized with at least one group chosen from hydrolyzed silyl groups and hydrolyzable silyl groups, as described above, wherein said composition provides a reshapable effect.

Another subject of the invention is a method of reshaping hair, comprising: (1) applying to the hair before, during, or after the initial shaping of the hairstyle, a composition comprising at least one silicon-containing polycondensate chosen from polyurethanes, polyureas, and polyurethane-ureas, such as a silylated polycondensate, a siliconated polycondensate, or a polycondensate that is functionalized with at least one group chosen from hydrolyzed silyl groups and hydrolyzable silyl groups, as described above, wherein said composition provides a reshapable effect, and (2) thereafter shaping the hairstyle at least once, wherein no additional composition or heat is added.

In one embodiment of the invention, such reshapable hair styling compositions may be in the form of a dispersion. The term "dispersion" means generally a two phase system where one phase contains discrete particles distributed throughout a bulk substance, the particles being the disperse or internal phase, and the bulk substance being the continuous or external phase. The continuous phase may be an aqueous phase and at least a portion of the polymer may exist as discrete particles. Dispersions are possible through the use of certain components that are insoluble in the aqueous system. By "dispersion," it is also meant that not necessarily the entire polymer needs to be water insoluble; some of the polymer can be soluble in the water mixture. It may be desirable that a dispersion remains stable under ambient conditions. In one embodiment, dispersions are stable at room temperature for more than 30 days, such as for more than 90 days, for more than 180 days, and for more than 360 days.

The phrase "silicon-containing polycondensate" means a polycondensate with at least one silicon atom present anywhere within the polycondensate. The silicon atom can be joined to any other atom. The term "hydrolyzable silyl group" means generally a silicon atom substituted with at least one moiety that will react with water to give a hydrolyzed silyl group. The term "hydrolyzed silyl group" means generally a silicon atom substituted with at least one —OH moiety. The inventors recognize that at some time after formation of a polycondensate that is functionalized with at least one group chosen from hydrolyzed silyl groups and hydrolyzable silyl groups, such as during the drying of the polymer, one or more —OH moieties may react further, such as, for example, forming an ≡Si—O—Si≡ group. Such products are encompassed within the phrase "polycondensate that is functionalized with at least one group chosen from hydrolyzed silyl groups and hydrolyzable silyl groups." A polycondensate that is functionalized with at least one silyl group, whether or not hydrolyzed or hydrolyzable, is also referred to as a silylated polycondensate in this document and such silylated polycondensates are a sub-genus of silicon-containing polycondensates. The at least one silyl group, whether or not hydrolyzed or hydrolyzable, may be terminal to and/or pendant from the polycondensate. The phrase "siliconated polycondensate" means a polycondensate containing necessarily at least one ≡Si—O—Si≡ group. Siliconated polycondensates are a subgenus of silicon-containing polycondensates.

The term "reshapable" hair styling composition means a hair styling composition providing hair styling that can be restored or modified without new material or heat being applied. For example, in order to restore or modify the hairstyle in case of "drooping" or loss of setting (dishevelment), no new materials, such as water or any form of fixing agent, or heat are required. Thus, to provide a "reshapable" effect means to provide a hair styling that can be restored or modified without new material or heat being applied. The efficacy of the composition can be long lasting, such as 10–24 hours, giving rise to a durable styling effect. Other terms, which may be synonymous with reshapable, include repositionable, remoldable, restyleable, rearrangable, and remodelable.

Various aqueous polycondensate dispersions comprising at least one hydrolyzable or hydrolyzed silyl group have been prepared by those skilled in the art. For example, U.S. Pat. Nos. 3,941,733; 3,983,291; 5,554,686; 5,756,633; 5,919,860; 5,952,445; 6,046,295; and 6,111,010, whose disclosures are incorporated herein in their entirety, disclose preparations of water-dispersed polyurethane-urea polycondensates terminated with silane functionality suitable for use as coatings for leather, paper, wood, metals, ceramics, stone, concrete, straw, glass, porcelain, textiles, and plastics, and for use as binders, adhesives, and impregnants. U.S. Pat. No. 4,567,228, whose disclosure is incorporated herein in its entirety, discloses aqueous dispersions of internally (i.e. pendant) silylated polycondensates and their use as coatings on hydroxyl-containing surfaces. U.S. Pat. No. 5,041,494, whose disclosure is incorporated herein in its entirety, discloses aqueous dispersions of polycondensates that have terminal and/or pendant silane functionality for use as a coating composition on organic or inorganic substrates including glass, wood, metals, plastics, leather, paper, building materials, stone and rock.

Although aqueous dispersions of silylated polycondensates of the invention have been widely disclosed, the inventors are not aware of any references to their use in reshapable hair styling compositions.

Processes and starting materials for preparing silylated polycondensates of the invention are disclosed in the references cited above. Suitable components for preparing the silylated polycondensates include polyisocyanates (such as diisocyanates); high molecular weight components (such as a polyol); low molecular weight chain extenders containing hydroxy, hydrazide, or amine groups; compounds containing ionic or nonionic hydrophilic groups; and compounds containing silyl groups. Chain terminators can optionally be included to control molecular weight and reduce cross-link density in the final polymer. Each component is discussed below in detail.

Another exemplary method for preparing a silylated polycondensate of the invention involves reacting at least one polyisocyanate with at least one polyol to form at least one isocyanate-terminated polycondensate prepolymer. The prepolymer can be chain extended followed by reaction with at least one compound containing silyl groups to form the silylated polycondensate. Additionally, the silylated polycondensate may be dispersed in a solvent through the use of external surfactants or by incorporating a hydrophilic group into the polymer. The resulting polymers may then be used to formulate various reshapable hair styling compositions.

As disclosed in U.S. Pat. No. 3,941,733, use of a distinct polyfunctional chain extender is not necessary to produce silylated polyurethane polycondensates. In some embodiments, the at least one hydrophilic component or the at least one silyl containing component may also function as the at least one polyfunctional chain extender.

Polyisocyanate Component

Any suitable organic polyisocyanate, including aliphatic, cycloaliphatic, arylaliphatic, and aromatic polyisocyanates, can be used alone or in combination to produce silicon-containing polycondensates of the invention, such as silylated polycondensates. While aromatic or aliphatic polyisocyanates are suitable, the aliphatic polyisocyanates may yield softer polymers and coatings that may have better light stability than the aromatic polyisocyanates. In one embodiment, the at least one polyisocyanate is a diisocyanate. Low levels of polyisocyanates containing more than two isocyanate groups in the molecule can be included without measurable changes in the characteristics of the resulting polymer.

In another embodiment, the at least one polyisocyanate may be chosen from dicyclohexylmethane 4,4'-diisocyanate (commonly referred to as $H_{12}MDI$), 1,3-bis(isocyanatomethyl) cyclohexane, 1,3-bis(1-isocyanato-1-methylethyl) benzene (commonly referred to as TMXDI), 3,5,5-trimethyl-1-isocyanato-3-isocyanatomethyl cyclohexane (commonly referred to as isophorone diisocyanate or IPDI), m-phenylene diisocyanate, p-phenylene diisocyanate, 2,4-tolylene diisocyanate, 2,6-tolylene diisocyanate, 4,4'-diisocyanato diphenylmethane (commonly referred to as MDI), benzidine diisocyanate, naphthalene-1,5-diisocyanate, hexamethylene diisocyanate (commonly referred to as HDI) and other alkylene diisocyanates (e.g., tetramethylene diisocyanate, decamethylene diisocyanate, and dodecamethylene diisocyanate), 4,4',4"-triphenylmethane triisocyanate, polyphenylmethylene polyisocyanates that are produced by phosgenation of aniline/formaldehyde condensation products containing up to about four aromatic rings, dianisidine diisocyanate, xylene diisocyanate, bis(2-isocyanatoethyl)fumarate, bis(2-isocyanatoethyl) cyclohex-4-ene-1,2-dicarboxylate, and bis (2-isocyanatoethyl) carbonate.

Polyol Component

In producing a silicon-containing polycondensate of the invention, such as a silylated polycondensate, at least one polyhydroxy compound, or polyol, may be used in a reaction with the at least one polyisocyanate, as described above.

In one embodiment, the at least one polyhydroxy compound may be chosen from (a) lactone polyols and alkylene oxide adducts thereof, (b) polyester polyols, and alkylene oxide adducts thereof, (c) polyoxyalkylene polyols, polyoxycycloalkylene polyols, and alkylene oxide adducts thereof, and (d) polytetramethylene glycols.

In another embodiment, the at least one polyol component may be chosen from diols. The term "diol" is intended to include mixtures of diols as well as mixtures containing low levels of triols or tetrols that do not excessively affect the properties of the final product. Exemplary diols may be chosen from polyester diols and polyoxyalkylene diols.

The term "alkylene oxide" includes, e.g., ethylene oxide, 1,2-epoxypropane, 1,2-epoxybutane, 2,3-epoxybutane, isobutylene oxide, epichlorohydrin, and the like and mixtures thereof.

Lactone polyols may be prepared by reacting a lactone, such as epsilon-caprolactone or a mixture of epsilon-caprolactone and an alkylene oxide, with a polyfunctional initiator such as a polyhydric alcohol. The term "lactone polyols" also includes the various copolymers such as lactone copolyesters, lactone polyester/polycarbonates, lactone polyester/polyethers, lactone polyester/polyether/ polycarbonates, and the like.

Polyester polyols are esterification products that range from liquids to non-crosslinked solids, i.e., solids that are soluble in many of the more common inert normally liquid organic media. Polyester polyols may be prepared by the reaction of polycarboxylic acids, their anhydrides, their esters, or their halides, with a stoichiometric excess of a polyol. Exemplary polycarboxylic acids that can be used to prepare a polyester polyol may be chosen from dicarboxylic acids and tricarboxylic acids, such as maleic acid, succinic acid, glutaric acid, adipic acid, pimelic acid, suberic acid, azelaic acid, sebacic acid, chlorendic acid, 1,2,4-butanetricarboxylic acid, phthalic acid, and the like. Esterification reactions are well known in the art.

Polyoxyalkylene polyols may be chosen from alkylene oxide adducts of, e.g., water, ethylene glycol, diethylene glycol, propylene glycol, dipropylene glycol, glycerol, 1,2, 6-hexanetriol, 1,1,1-trimethylol ethane or propane, pentaerythritol, and the like. The alkylene oxides used in producing polyoxyalkylene polyols normally have from 2 to 4 carbon atoms. In one embodiment, the alkylene oxide is chosen from ethylene oxide, propylene oxide, and mixtures thereof.

Another useful class of polyols is the polyoxytetramethylene glycols, which may be prepared by polymerizing tetrahydrofuran in the presence of an acidic catalyst.

The molecular weight of the at least one polyol component may be one significant factor in determining the final properties of the polymer. Generally, the higher the molecular weight, the softer the resulting polymer. The term "molecular weight" is used herein to refer to the number average molecular weight ($M_n$). In one embodiment, polyols of molecular weight as low as 200 and as high as 5000 may produce suitable silicon-containing polycondensates of the invention, for example silylated polycondensates, such as polyols with a molecular weight ranging from 300 to 3000, which are readily commercially available. Polyols of lower molecular weight can be used as the at least one polyfunctional chain extender as discussed below.

Polyfunctional Chain Extender Component

As used herein the term "polyfunctional chain extender" means a polyactive hydrogen compound having a functionality of about 2 to about 4, such as from about 2 to about 3, and further such as about 2 and generally having a molecular weight ranging from about 30 to about 2000, such as from about 30 to about 1000.

In one embodiment, the at least one polyfunctional chain extender may be chosen from polyfunctional alcohols, amines, and carboxylic acid hydrazides. In another embodiment, the at least one polyfunctional chain extender may be chosen from polyfunctional amines and carboxylic acid hydrazides. Useful polyamines may include ethylenediamine, 1,6-diaminohexane, piperazine, tris(2-aminoethyl)amine, and amine terminated polyethers such as JEFFAMINE D230 and JEFFAMINE D400, from the Huntsman Corporation, Salt Lake City, Utah, USA. Useful carboxylic acid hydrazides may include adipic acid dihydrazide and oxalic acid dihydrazide. Useful polyfunctional alcohols may include alkylene diols having 2 to 24 carbon atoms such as ethylene glycol, diethylene glycol, 1,4-butane diol, 1,8-octane diol, and 1,2-decandiol.

Other useful chain extenders may include polythiols such as 1,2-ethanedithiol, 1,4-butanedithiol, 2,2'-oxytris(ethane thiol), and di- and tri-mercaptopropionate esters of poly(oxyethylene) diols and triols. Water may also be useful as a polyfunctional chain extender as it reacts with isocyanate to form an unstable carbamic acid, which loses carbon dioxide to liberate an amine. This amine is then available to react with another isocyanate.

Hydrophilic Component

In one embodiment, the silicon-containing polycondensate of the invention, such as a silylated polycondensate, may be dispersed in a solvent through the use of external surfactants or by incorporating a hydrophilic group into the polymer. The latter may be achieved using at least one hydrophilic component having at least one water solubilizing group and at least one isocyanate reactive functional group. The at least one hydrophilic component may act to stabilize the polycondensate dispersion in an aqueous solvent system. Suitable hydrophilic components may be chosen from groups that contain an ionic group, groups that contain at least one moiety capable of forming an ionic group, and groups that contain nonionic water-soluble groups such as polyethylene glycol and its copolymers with propylene glycol.

When present, the ionic group of the at least one hydrophilic component can be cationic, anionic, or zwitterionic. The cationic groups may originate from the at least one isocyanate or the at least one polyol component but most conveniently are added in as the at least one polyol component. In one embodiment, the cationic group may be incorporated directly into the prepolymer. For example, a quaternary diol such as VARIQUAT 1215 may be reacted into the prepolymer directly. In an alternative embodiment, a precursor group may be reacted into the prepolymer and then may be rendered cationic in a subsequent reaction. For example, active hydrogen functional tertiary amines such as methyldiethanolamine and its polyethoxylated adducts may be incorporated into the prepolymer backbone and subsequently protonated with a mineral or organic acid to form an ionic salt or alkylated to form a quaternary ammonium group. The reaction of the incorporated tertiary amine with hydrogen peroxide, propane sultone, or lactone is one method that may yield suitable zwitterionic moieties.

In one embodiment, stabilizing cationic components may be water soluble, i.e., generally having a solubility in water of at least 1% by weight, such as in excess of 10% by weight. Such stabilizing cationic compounds may have the following structure:

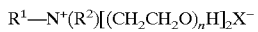

where
- $R^1$ is a group chosen from $C_1$ to $C_{18}$ alkyls, $C_6$ to $C_{18}$ aryls, and $C_6$ to $C_{18}$ arylalkyls optionally substituted in and/or on the chain by at least one atom chosen from N, O, and S atoms;
- $R^2$ is a group chosen from a hydrogen atom and $C_1$ to $C_{18}$ alkyls;
- n is an integer ranging from about 1 to about 200, such as from about 1 to about 50 and further such as from about 1 to about 20; and
- $X^-$ is chosen from halides, sulfates, methosulfates, ethosulfates, acetates, carbonates, and phosphates.

In one embodiment, cationic stabilizing compounds may be chosen from protonated and alkylated methyl diethanol amines as well as PEG 2 cocomonium chloride and PEG-15 cocomonium chloride available from CKWitco, Greenwich, Conn., USA as VARIQUAT 638 and VARIQUAT K1215 respectively.

It is possible to incorporate cationic compounds that have a single reactive hydrogen group.

In one embodiment, the anionic stabilizer may be present on either the at least one isocyanate component or the at least one polyol component. In another embodiment, the anionic group may be chosen from sulfonates, phosphonates, phosphates, and carboxylates, such as for example from sulfonates and carboxylates, and further such as, for example, from sulfonates. The sulfonates may be chosen from the sulfonated polyols described in U.S. Pat. No. 4,738,992 (Larson et al.), whose disclosure is incorporated herein in its entirety by reference. In one embodiment, the sulfonate may be chosen from polyesterdiols having the following structure:

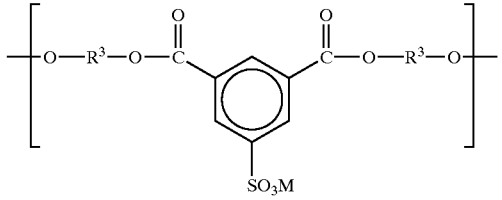

wherein M is a cation chosen from H, Na, K, Li, alkaline earth metals, and primary, secondary and tertiary ammonium cations, such as ammonium, methylammonium, butylammonium, diethylammonium, triethylammonium, tetraethylammonium, and benzyltrimethylammonium cations; each $R^3$ is independently chosen from divalent aliphatic groups having an average molecular weight ranging from about 200 to about 600 and comprising at least one ether and/or ester functional group, which may be chosen from:
- —$CH_2CH_2$—($OCH_2CH_2$—)$_n$—,
- —$CH(CH_3)CH_2$—($OCH(CH_3)CH_2$—)$_n$—,
- —$(CH_2)_4$—$(O(CH_2)_4)_n$—, and
- —$(CH_2)_mCO$—$[O(CH_2)_mCO]_n$— groups;
  where m is an integer ranging from about 2 to about 5 and n is an integer ranging from about 2 to about 15.

Suitable carboxylate and carboxylic acid functional polyols may include polyols chosen from dimethylolpropionic acid and its polyethoxylated derivatives as well as acid grafted polyethers such as the UCARMOD polyols available from Union Carbide Specialty Chemicals Div., Danbury, Conn. Carboxy functional polyamines, such as lysine and histidine may also be useful. In one embodiment, these polyols can be neutralized with an organic or inorganic base either before or after preparation of the at least one isocyanate terminated polycondensate prepolymer.

In one embodiment, the addition of an external surfactant to the polycondensate is used instead of or in combination with the incorporation of a hydrophilic group into the polymer. Suitable surfactants may be chosen from cationic, anionic, nonionic, and amphoteric (such as zwitterionic) surfactants. The surfactants may be present in an amount sufficient to disperse the silicon-containing polycondensate of the invention, such as a silylated polycondensate, in a solvent, including water.

Silyl Containing Component

At least one silyl group may be incorporated into the polycondensate of the invention terminally (at the ends) and/or internally (pendant from the backbone). When incorporated terminally, a component containing at least one silyl group and at least one electrophilic or nucleophilic reactive group may be used. For example, a prepolymer terminated with isocyanate can be reacted with a silane functionalized with an alkyl amine, hydroxyl, or thiol. Suitable silanes that may react with isocyanates may be chosen from, but are not limited to, the following compounds:

$H_2NCH_2CH_2CH_2Si(OC_2H_5)_3$,
$HN(CH_2CH_2CH_2Si(OC_2H_5)_3)_2$,
$HSCH_2CH_2CH_2Si(OCH_3)_3$,
$HO(C_2H_4O)_3C_2H_4N(CH_3)(CH_2)_3Si(OC_4H_9)_3$,
$H_2NCH_2C_6H_4CH_2CH_2Si(OCH_3)_3$,
$HSCH_2CH_2CH_2Si(OCOCH_3)_3$,
$H_2NCH_2CH_2CH_2Si(OCH_3)_3$,

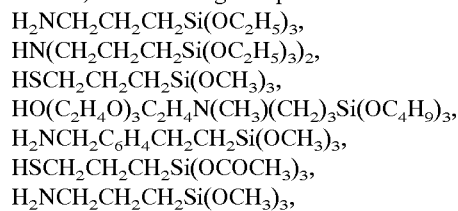

$HN(CH_3)CH_2CH_2Si(OCH_3)_3$, and
$HSCH_2CH_2CH_2SiCH_3(OCH_3)_2$.

Conversely, a prepolymer terminated with an amine or a hydroxyl moiety can be reacted with a component containing a silane that is functionalized with an alkyl isocyanate such as 3-isocyanatopropyltriethoxysilane, and $OCNCH_2CH_2CH_2Si(OCH_3)_3$.

When incorporated internally, a component containing at least one silyl group and at least two isocyanate or isocyanate reactive groups may be used. For example, silanes functionalized with two hydroxyls or two amines may be used as both the at least one silyl containing component and the at least one chain extender, placing silane functionality internally. In one embodiment, silane that is functionalized with an alkyl isocyanate with two reactive sites may be chosen from:

$(HOC_2H_5)_2NC_3H_6Si(OCH_3)_3$, and
$H_2NCH_2CH_2CH_2NHCH_2CH_2CH_2Si(OCH_3)_3$.

A silane with only one electrophilic or nucleophilic group can be used, provided that the polymer possesses a companion nucleophilic or electrophilic group along its backbone. For example, a pendant carboxylic acid functionality on the polymer chain may be reacted with an alkyl epoxy silane such as 3-glycidoxypropyltrimethoxysilane.

Other methods of incorporating silyl groups are known in the art, such as hydrosilation of a pendant or terminal olefin with a trialkoxysilane hydride.

Silane compounds containing two or three hydrolyzable groups on the silicon atom (as $X_2Si=$ or $X_3Si$—) and one or two organic groups are suitable for forming the silyl groups. The "X" can be any of the conventional hydrolyzable groups, such as hydrogen, alkoxy, acyloxy, halogen, amino, oxime, and the like.

In one embodiment, a silane compound containing one or no hydrolyzable groups on the silicon atom may be suitable for forming the silyl groups; however, such compounds often lack commercial availability, have slower reactivity, and lower cross-linking efficiency than silane compounds containing two or three hydrolyzable groups on the silicon atom.

In one embodiment, the silane compound may be chosen from those with the structure:

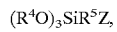

$(R^4O)_3SiR^5Z$, wherein $(R^4O)_3SiR^5$— is a silyl moiety; $R^4$ is a radical chosen from $C_1$ to $C_4$ alkyls, such $C_1$ to $C_2$ alkyls (i.e., methoxy, ethoxy), and $C_2$ to $C_5$ acyls, such as $C_2$ to $C_3$ acyls (i.e., acetyl or propionyl); $R^5$ is radical chosen from divalent $C_2$ to $C_{20}$ organic bridging radicals, such as $C_3$ to $C_{10}$ organic bridging radicals, wherein the organic bridging radicals are chosen from (1) divalent hydrocarbyl radicals and free from isocyanate-reactive groups, (2) divalent oxyalkylene radicals, such as mono- or poly-oxyalkylene radicals containing not more than one ether oxygen per two carbon atoms, and (3) divalent hydrocarbylamino radicals. Z is either a nucleophilic group such as —OH, —SH, —NHR, —NH$_2$, and —N(C$_2$H$_4$OH)$_2$ or an electrophilic group such as —NCO and epoxide. Representative divalent organic radicals include —CH$_2$CH$_2$—, —CH$_2$CH$_2$CH$_2$—, —CH$_2$CH$_2$CH$_2$OCH$_2$CH$_2$—, —CH$_2$CH$_2$CH$_2$NHCH$_2$CH$_2$—, and —CH$_2$CH$_2$C$_6$H$_4$CH$_2$CH$_2$—. Such silicon-containing compounds are well known in the art and many are commercially available or are readily prepared.

While not being limited to theory, it is believed that a chain-extended silylated polycondensate of the invention may be cured by hydrolysis of the silyl group and formation of siloxane linkages. This reaction probably may begin as soon as the polymer is exposed to water, but generally proceeds slowly at room temperature and within a pH range of about 6.5 to about 9. The reaction proceeds more rapidly after drying and is accelerated in the presence of acidic or basic catalysts. The formation of siloxane linkages crosslinks the film formed from the polymer. These crosslinks are distinguished from crosslinks and branching that may form in low concentration from the use of triols, triisocyanates, tetrols, and other highly functional reactants in preparing the prepolymer. The latter crosslinks are herein sometimes referred to as prepolymer-derived crosslinks and are to be understood as the type of crosslinks present before curing.

Chain Terminator Component

As used herein the term "chain terminator" means an active hydrogen compound having a functionality of about 1 and generally having a number average molecular weight ranging from about 30 to about 2000, such as from about 30 to about 1000. In one embodiment, a chain terminator component may be included during preparation of the prepolymer or added during the dispersion and chain extension steps. Chain terminators may be chosen from monofunctional alcohols, amines, and carboxylic acid hydrazides. When chain termination is done during the dispersion step, the chain terminator may be chosen from monofunctional amines, because the isocyanate functional moieties will selectively react with them in the presence of water. Useful amines include butyl amine and 2-amino-2-methyl-1-propanol. Useful monofunctional alcohols include those having 2 to 24 carbon atoms such as ethanol, butanol, octanol, cetyl alcohol, and stearyl alcohol.

Dispersion Techniques

Aqueous dispersions of some silicon-containing polycondensates of the invention may be prepared in accordance with the methods known in polyurethane chemistry and described, e.g., in "Waterborne Polyurethanes," Rosthauser et al, Advances in Urethane Science and Technology, Vol. 10, pg. 121–162 (1987), whose disclosure is incorporated by reference in its entirety herein.

These methods generally involve subjecting the silicon-containing polycondensate to a high shear process in the presence of an aqueous carrier. Microfluidization is one such process for making stable uniform sub-micron dispersions, including dispersions of silicon-containing polycondensate. The process uses high-pressure liquid jet milling to combine water dispersible polymers with water. In one embodiment, the silylated polycondensate of the invention has a viscosity in the range of 1 to 500,000 centipoises as measured by a standard Brookfield viscometer with an appropriate spindle and speed to achieve a reading between 20–80 at a room temperature of about 25° C. When higher viscosity is encountered, an organic solvent may be added to reduce the viscosity to the desired range. In the microfluidization process, the silicon-containing polycondensate or a solution of silicon-containing polycondensate in an organic solvent can be injected into a water stream and then subjected to high pressure of 0.6 to 300 MPa (100 to 40,000 psi) liquid jet milling in interaction chambers. The interaction chambers, which provide a high shear zone, are generally configured to be explosive expansion chambers, or use high velocity impinging streams, or contain orifices in series having decreasing diameters. In this process, all of the liquid is forced through the interaction chamber configurations providing uniform shear for all the material.

When organic solvent is used to aid in preparation of the silicon-containing polycondensate and reduce viscosity, this solvent may be miscible with water allowing for dispersion into an aqueous solution. If an organic solvent having a boiling point lower than 100° C. has been used, the organic solvent may be evaporatively removed to leave an essentially aqueous polymer dispersion of the silicon-containing polycondensate. Representative organic solvents useful for this process may be chosen from acetone, methyl ethyl ketone, and tetrahydrofuran. An organic solvent that has a boiling point greater than 100° C. (referred to as "high boiling solvent" for convenience) can also be used. When used, the preparation should be conducted in as concentrated solution as possible, e.g., preferably equal to or less than 20 weight percent solvent to minimize the amount present in the dispersion. Such high boiling solvents should be chosen from materials that do not have toxicity or irritancy concerns in cosmetic applications. Of course, solvents with boiling points lower than 100° C., such as ethanol, can optionally be included in the final formulation to provide benefits such as fast-drying.

According to one process for preparing a silylated polyurethane-urea dispersion, at least one isocyanate-functional prepolymer is prepared, chain extended and/or chain terminated to form a silylated polyurethane-urea and subsequently dispersed in water. This process is disclosed in U.S. Pat. No. 3,479,310, whose disclosure is incorporated in its entirety herein by reference.

When amines are reacted with the at least one isocyanate-functional prepolymer, either as chain terminators or chain extenders, one method of preparing a dispersion is by dispersing the prepolymer in water and then reacting the prepolymer with the amino group-containing compounds, which may be mixed with water either before, during, or after dispersing the at least one isocyanate-functional prepolymer.

The amount of amino group-containing compounds to be used in accordance with the present invention is dependent upon the number of isocyanate groups in the prepolymer. Generally, the ratio of isocyanate groups to amino groups ranges from 1.0:0.6 to 1.0:1.1, such as from 1.0:0.8 to 1.0:0.98, on an equivalent basis.

The reaction between the at least one isocyanate-functional prepolymer and the amino group-containing compounds is generally conducted at temperatures ranging from about 5° C. to about 90° C., such as from about 20° C. to 80° C., and further such as from about 30° C. to 60° C. The reaction conditions are normally maintained until the isocyanate groups are essentially completely reacted.

In one embodiment, the final product is a stable, aqueous dispersion of silicon-containing polycondensate particles having a solids content of up to about 60%, such as about 15% to about 60%, and further such as about 30% to about 45% by weight. A dispersion is deemed stable so long as the discrete particles of the internal phase remain distributed throughout the bulk substance (external phase). It is always possible, however, to dilute the dispersions to any minimum solids content desired. The average particle size of the silicon-containing polycondensate of the invention generally may be below about 1.0 micron, such as about 0.001 to about 0.5 microns and further such as about 0.01 to about 0.3 microns. The small particle size may enhance the stability of the dispersed particles and may also lead to films with high surface gloss.

In one embodiment, the dispersions may be blended with other dispersions or with other known additives such as fillers, plasticizers, pigments (such as carbon black), silica sols and other known leveling agents, wetting agents, antifoaming agents, and stabilizers.

In another embodiment, the silicon-containing polycondensate of the invention is in a cosmetically acceptable vehicle. The appropriate cosmetically acceptable vehicle is adapted to the method of application selected. The vehicle preferably comprises an appropriate solvent, including water, to which may be added additives such as gelling agents, foaming agents, and silicones.

It is understood that the person skilled in the art will know how to choose the additional additives and their amount in the composition according to the invention, such as the constituents of the vehicle, so as not to adversely affect or substantially affect its reshapable hair styling properties.

In yet another embodiment of the invention, the silicon-containing polycondensate of the invention has a glass transition temperature (Tg) ranging from about −100° C. to about 15° C. According to the present invention, the Tg of the silicon-containing polycondensate is obtained following the application of the silicon-containing polycondensate in a simplex vehicle to a substrate and then drying. The glass transition temperature is determined by the Differential Scanning Calorimetric method (DSC).

The composition according to the invention may comprise at least one other constituent, which is conventional in cosmetics, chosen from preservatives; perfumes; active hair care agents; plasticizers; anionic, cationic, amphoteric (such as zwitterionic), and nonionic surfactants; hair conditioning agents such as silicone fluids, fatty esters, fatty alcohol, long chain hydrocarbons, emollients, lubricants, and penetrants such as lanolin compounds, protein hydrolysates, and other protein derivatives; anionic, cationic, amphoteric (such as zwitterionic), and nonionic polymers; dyes; tints; bleaches; reducing agents; pH adjusting agents; sunscreens such as UV filters; and thickening agents.

The compositions according to the invention can be provided in any form known from the prior art, which is appropriate for their application to the hair, including in the form of a vaporizable composition such as sprays and aerosols, mousse, gel, stick, mud, or lotion.

The composition may be in any of the conventional forms of cosmetic composition including, but not limited to, shampoos, hair rinses, permanent waving compositions, waving compositions, hair dye compositions, hair straightening compositions, hair fixing products, hair styling gel products, products to use before or after a hair dye treatment, products to use before or after a permanent waving treatment, hair straightening compositions, products to use before or after a hair straightening treatment, and fixing foams.

The composition according to the invention may be vaporizable, for example by a pump, or may be a pressurized aerosol composition. It may be vaporizable by a dispensing valve controlled by a dispensing head, which in turn comprises a nozzle, which vaporizes the aerosol composition. A vaporizable composition according to the invention comprises an appropriate solvent. Advantageously, the appropriate solvent comprises at least one solvent chosen from water and lower alcohols. In accordance with the invention, the term lower alcohol means a $C_1$ to $C_4$ aliphatic alcohol, preferably ethanol.

When the vaporizable composition according to the invention is an aerosol composition, it additionally comprises an appropriate amount of propellant. The propellant comprises compressed or liquefied gases, which are normally employed for the preparation of aerosol compositions. Suitable gasses include compressed air, carbon dioxide, nitrogen, and gases, such as dimethyl ether, fluorinated or non-fluorinated hydrocarbons, and mixtures thereof.

The present invention additionally provides an aerosol device comprising a vessel comprising an aerosol composition, which comprises on the one hand a liquid phase (or juice) comprising at least one hair styling material as described above in an appropriate medium and on the other hand a propellant, and a dispenser for dispensing said aerosol composition.

The present invention additionally provides a method of treating keratinous fibers, especially hair, in which the composition according to the invention as defined above is applied to the hair before, during, or after the shaping of the hairstyle.

The compositions according to the invention can be rinsed off or not rinsed off the hair.

The present invention additionally provides the use of a composition as defined above in, or for the preparation of, a cosmetic reshapable hair styling formulation.

The determination of whether a composition with a silicon-containing polycondensate according to the invention can provide a reshapable effect can be determined by an in vivo test.

Where the composition is in the form of a lotion, for example, the in vivo test proceeds as follows. The hair of the model is washed and then divided into two symmetrical portions, the right and the left sides. The composition is applied to one side of the head of the model, while a reference composition is applied to the other side of the head. The reference composition may, for example, be chosen from water, an existing commercial product, or another composition under study. The hairdresser dries and styles both sides of the head. The two sides of the head are separately evaluated for the styling effect, the cosmetic properties, and the reshapable effect. For example, once dried, the hair is brushed in different directions to remove the original styling. The hair is then brushed to restore the original styling. The process of removing the styling, restoring the styling, and evaluating the success of restoring the styling is repeated at least one more time to determine whether the composition is a reshapable hair styling composition. A reshapable hair styling composition permits (1) the original hair styling to be restored after brushing and (2) the creation of a new hair styling after brushing, which may also be restored after brushing. If the composition to be evaluated is in another form, such as a shampoo or conditioner, the in vivo test can be appropriately modified by one skilled in the art.

It is understood that the person skilled in the art would recognize that not all formulations would provide reshapable effect for all hair types during in vivo testing and will know how to formulate and evaluate reshapable hair styling composition in view of the various hair parameters, such as length (short versus long), diameter (thin versus thick), structure (curly versus straight), condition (oily, dry, or normal); and whether the hair is colored, bleached, permed, or straightened. Thus, in vivo testing may require testing on 10–20 different individuals.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The invention may be understood more clearly with the aid of the non-limiting examples that follow, and which constitute an advantageous embodiment of the compositions in accordance with the invention.

EXAMPLES

Several reshapable hair styling compositions according to the invention were produced with different silicon-containing polycondensates. Percentages given are by weight, unless otherwise specified. Abbreviations and sources for the components used to manufacture silicon-containing polycondensates of the invention are disclosed in the Table.

| Components | Manufacturer |
| --- | --- |
| Acetone | J. T. Baker, Inc., Phillipsburgh, NJ |
| Butylamine | Aldrich Chemical Co., Milwaukee, WI |
| Dibutyltin dilaurate (DTDL) | Aldrich Chemical Co., Milwaukee, WI |
| Diethylene glycol | Aldrich Chemical Co., Milwaukee, WI |
| Ethylene glycol (EG) | Aldrich Chemical Co., Milwaukee, WI |
| Isophorone diisocyanate (IPDI) | Aldrich Chemical Co., Milwaukee, WI |
| Methyl ethyl ketone (MEK) | J. T. Baker, Inc., Phillipsburgh, NJ |

-continued

| Components | Manufacturer |
| --- | --- |
| Polycaprolactone diol | Tone 0201 ™ diol, Union Carbide, Dansbury, CT |
| Polycaprolactone sodium sulfo isophthalate (PCPSSIP) | Prepared according to Example 29 of U.S. Pat. No. 5,929,160 |
| Triethylamine | Aldrich Chemical Co., Milwaukee, WI |
| 1,2-decanediol | Aldrich Chemical Co., Milwaukee, WI |
| 1,6-diisocyanatohexane | Aldrich Chemical Co., Milwaukee, WI |
| 2,2'-bis(hydroxymethyl)-propionic acid | Aldrich Chemical Co., Milwaukee, WI |
| 3-aminopropyltriethoxysilane | Aldrich Chemical Co., Milwaukee, WI |
| 4,4'-diisocyanato dicyclohexylmethane | Aldrich Chemical Co., Milwaukee, WI |

1) Preparation of the Silicon-containing Polycondensates

Example 1

Preparation of Silanol-terminated Polyurethane-urea in Water

A mixture of PCPSSIP (349.7 g and 0.47 mol, based on a hydroxyl equivalent weight of 370 for the mixture), polycaprolactone diol (39.3 g, 0.08 mol), ethylene glycol (69.9 g, 1.13 mol), diethylene glycol (23.9 g, 0.23 mol), IPDI (450.1 g, 2.03 mol), DTDL (0.90 g, 1.4 mmol), and MEK (502 g) was charged to a vessel equipped with stirring and heated to 80° C. After 4 hours, a solution of 3-aminopropyltriethoxysilane (49.9 g, 0.23 mol) in MEK (473 g) was added to the reaction mixture, which was maintained at 80° C. for an additional 15 minutes. Water (975 g) was added to the reaction mixture over a 15 minute period with vigorous stirring and MEK was subsequently distilled from the mixture under reduced pressure to produce a dispersion (50% solids) of a silanol-terminated polyurethane-urea in water.

Example 2

Preparation of Silanol-terminated Polyurethane-urea in Water

A mixture of 1,2-decanediol (69.71 g, 0.40 mol), 1,6-diisocyanatohexane (102.94 g, 0.61 mol), DTDL (0.27 g, 0.4 mmol), and acetone (161 mL) was heated with stirring to 55° C. After 2 hours, PCPSSIP (125.8 g, 0.17 mol based on a hydroxyl equivalent weight of 370 for the mixture) was added, and the mixture was heated for 2 additional hours at 55° C. A solution of 3-aminopropyltriethoxy silane (9.79 g, 0.044 mol) in acetone (144 mL) was added to the reaction mixture, which was maintained at 55° C. for an additional 15 minutes. Water (500 mL) was added to the reaction mixture over a 15 minute period with vigorous stirring and acetone was subsequently distilled from the mixture under reduced pressure to produce a dispersion of a silanol-terminated polyurethane-urea in water. Modulated differential scanning calorimetry (MDSC) analysis made of a film of the dispersion indicated that the polymer had a $T_g$ of −17° C.

Example 3

Preparation of Silanol-terminated Polyurethane-urea in Water

A mixture of 1,2-decanediol (34.86 g, 0.20 mol), 1,6-diisocyanatohexane (51.47 g, 0.31 mol), DTDL (0.14 g, 0.2 mmol), and acetone (80 mL) was heated with stirring to 55° C. After 2 hours, PCPSSIP (62.9 g, 0.09 mol based on a hydroxyl equivalent weight of 370 for the mixture) was added, and the mixture was heated for 2 additional hours at 55° C. A solution of 3-aminopropyltriethoxysilane (20.6 g, 9.3 mmol) and butylamine (0.45 g, 6.2 mmol) in acetone (69 mL) was added to the reaction mixture, which was maintained at 55° C. for an additional 15 minutes. Water (240 mL) was added to the reaction mixture over a 15 minute period with vigorous stirring and acetone was subsequently distilled from the mixture under reduced pressure to produce a dispersion of a silanol-terminated polyurethane-urea in water.

Example 4

Preparation of Silanol-terminated Polyurethane-urea in Water

A mixture of 1,2-decanediol (22.05 g, 0.13 mol), 1,6-diisocyanatohexane (32.56 g, 0.19 mol), DTDL (0.09 g, 0.1 mmol), and acetone (51 mL) was heated with stirring to 55° C. After 2 hours, PCPSSIP (0.05 mol based on a hydroxyl equivalent weight of 370 for the mixture) was added, and the mixture was heated for 2 additional hours at 55° C. A solution of 3-aminopropyltriethoxysilane (1.97 g, 8.9 mmol) and butylamine (0.22 g, 3.0 mmol) in acetone (45 mL) was added to the reaction mixture, which was maintained at 55° C. for an additional 15 minutes. Water (160 mL) was added to the reaction mixture over a 15 minute period with vigorous stirring and acetone was subsequently distilled from the mixture under reduced pressure to produce a dispersion of a silanol-terminated polyurethane-urea in water.

Example 5

Preparation of Silanol-terminated Polyurethane-urea in Water

A mixture of 1,2-decanediol (24.28 g, 0.12 mol), 1,6-diisocyanatohexane (31.79 g, 0.19 mol), DTDL (0.08 g, 0.1 mmol), and acetone (52 mL) was heated with stirring to 55° C. After 2 hours, PCPSSIP (40.9 g, 0.06 mol based on a hydroxyl equivalent weight of 370 for the mixture) was added, and the mixture was heated for 2 additional hours at 55° C. A solution of 3-aminopropyltriethoxysilane (1.12 g, 5.1 mmol) and butylamine (0.37 g, 5.1 mmol) in acetone (45 mL) was added to the reaction mixture, which was maintained at 55° C. for an additional 15 minutes. Water (130 mL) was added to the reaction mixture over a 15 minute period with vigorous stirring and acetone was subsequently distilled from the mixture under reduced pressure to produce a dispersion of a silanol-terminated polyurethane-urea in water.

Example 6

Preparation of Silanol-terminated Polyurethane-urea in Water

A mixture of 1,2-decanediol (27.88 g, 0.16 mol), 1,6-diisocyanatohexane (41.18 g, 0.24 mol), DTDL (0.11 g, 0.2 mmol), and acetone (64 mL) was heated with stirring to 55° C. After 2 hours, PCPSSIP (50.32 g, 0.07 mol based on a hydroxyl equivalent weight of 370 for the mixture) was added, and the mixture was heated for 2 additional hours at 55° C. A solution of 3-aminopropyltriethoxysilane (2.15 g, 9.7 mmol) and butylamine (0.30 g, 4.2 mmol) in acetone (55 mL) was added to the reaction mixture, which was maintained at 55° C. for an additional 15 minutes. Water (176 mL) was added to the reaction mixture over a 15 minute period with vigorous stirring and acetone was subsequently distilled from the mixture under reduced pressure to produce a dispersion of a silanol-terminated polyurethane-urea in water.

Example 7

Preparation of Silanol-terminated Polyurethane-urea in Water

A mixture of PCPSSIP (555 g, 0.75 mol based on a hydroxyl equivalent weight of 370 for the mixture), IPDI (190.1 g, 0.86 mol), DTDL (0.36 g, 0.56 mmol), and acetone (400 g) was heated with stirring to 55° C. After 8 hours, a solution of 3-aminopropyltriethoxysilane (45.3 g, 0.20 mol) in acetone (365 g) was added to the reaction mixture, which was maintained at 55° C. for an additional 15 minutes. Water (1700 g) was added to the reaction mixture over a 15 minute period with vigorous stirring and acetone was subsequently distilled from the mixture under reduced pressure to produce a dispersion (33% solids) of a silanol-terminated polyurethane-urea in water. MDSC analysis made of a film of the dispersion indicated that the polymer had a $T_g$ of $-20°$ C.

Example 8

Preparation of a Carboxylated Polyurethane-urea Dispersion

A mixture of 2,2'-bis(hydroxymethyl)propionic acid (20.1 g, 0.150 mol), polycaprolactone diol (262 g, 0.50 mol), IPDI (159 g, 0.72 mol), MEK (237 g), and DTDL (0.30 g, 0.05 mmol) was heated at reflux for 5 hours, then left at room temperature for 72 hours. The mixture was then heated at reflux for 6 more hours. An aliquot was removed for determination of isocyanate equivalent weight as described in Example 29 of U.S. Pat. No. 5,929,160, whose disclosure is incorporated herein in its entirety. Based on the found isocyanate equivalent weight of 3,607, a solution of triethylamine (14.2 g, 0.141 mol) and 3-aminopropyltriethoxysilane (24.9 g, 0.11 mol) in MEK (232 g) was added to the reaction mixture. After stirring for an additional 15 minutes, water (1350 g) was added to the solution, and then the MEK was distilled from the mixture at reduced pressure to produce a 28% solids dispersion of the carboxylated silicon-containing polyurethane-urea in water.

Example 9

A 50/50 mixture of the dispersion from Example 4 and a dispersion comprising AQ 1350 by the Eastman Chemical Co. as disclosed in WO 98/38969 can be made.

Example 10

A 25/75 mixture of the dispersion from Example 6 and the dispersion from Example 7 can be made.

2) Preparation of the Hair Styling Compositions

Four hair styling compositions were prepared using the components and amounts in weight percent listed hereafter. The testing was conducted on several models with one part of the head receiving a reference composition and the other side of the head receiving the tested composition. The compositions were applied to wet hair after shampooing. In some instances, the composition was rinsed off after application. The hair was then dried, brushed, and evaluated.

Reference

AQ 1350 4% active material

Water qsp 100%

Formulation A:

Example 5 4% active material

Water qsp 100%

Formulation A imparted better hairstyling with better cosmetic properties than the reference. The reshapable effect was found, which was equal to the reference.

Formulation B:

Example 6 4% active material

Water qsp 100%

Formulation B imparted better hairstyling and volume than the reference; however, the cosmetic properties and the reshapable effect, while present, were not as good as the reference.

Formulation C:
Example 5 4% active material
Water qsp 100%
Formulation C, when rinsed, imparted better hairstyling with better cosmetic properties than the reference; however, the reshapable effect, while present, was not as good as the reference.
Formulation D
Example 6 4% active material
Water qsp 100%
Formulation D, when rinsed, imparted better cosmetic properties than the reference; however, the hairstyling and the reshapable effect, while present, were not as good as the reference.

What is claimed is:

1. A reshapable hair styling composition comprising at least one silicon-containing polycondensate chosen from polyurethanes, polyureas, and polyurethane-ureas, wherein said composition provides a reshapable effect.

2. The composition according to claim 1, wherein said at least one silicon-containing polycondensate is in the form of a dispersion.

3. The composition according to claim 2, wherein said at least one silicon-containing polycondensate is in the form of an aqueous dispersion.

4. The composition according to claim 1, wherein said at least one silicon-containing polycondensate is in a cosmetically acceptable vehicle.

5. The composition according to claim 1, wherein said at least one silicon-containing polycondensate has a Tg ranging from about −100° C. to about 15° C.

6. The composition according to claim 1, further comprising at least one additional polymer.

7. The composition according to claim 6, wherein said at least one additional polymer is chosen from anionic, cationic, amphoteric, and nonionic polymers.

8. The composition according to claim 1, further comprising at least one conventional cosmetic constituent chosen from preservatives, perfumes, active hair care agents, plasticizers, anionic, cationic, amphoteric, and nonionic surfactants, hair conditioning agents, silicone fluids, fatty esters, fatty alcohol, long chain hydrocarbons, emollients, lubricants, penetrants, lanolin compounds, protein hydrolysates, other protein derivatives, dyes, tins, bleaches, reducing agents, pH adjusting agents, sunscreens, and thickening agents.

9. A composition according to claim 1, wherein said reshapable hair styling composition is in the form of a spray, aerosol, mousse, gel, stick, mud, or lotion.

10. A reshapable hair styling composition comprising at least one silylated polycondensate chosen from polyurethanes, polyureas, and polyurethane-ureas, wherein said composition provides a reshapable effect.

11. A composition according to claim 10, wherein said at least one silylated polycondensate is the product of reactants comprising:
(a) at least one isocyanate terminated polycondensate prepolymer; and
(b) at least one silyl containing component.

12. The composition according to claim 10, wherein said at least one silylated polycondensate is in the form of a dispersion.

13. The composition according to claim 12, wherein said at least one silylated polycondensate is in the form of an aqueous dispersion.

14. The composition according to claim 11, wherein said at least one isocyanate terminated polycondensate polymer is the product of reactants comprising:
(i) at least one polyisocyanate and
(ii) at least one polyol.

15. The composition according to claim 14, wherein, wherein said at least one polyisocyanate is chosen from diisocyanates.

16. The composition according to claim 14, wherein said at least one polyisocyanate is chosen from dicyclohexylmethane 4,4'-diisocyanate, 1,3-bis(isocyanatomethyl) cyclohexane, 1,3-bis(1-isocyanato-1-methylethyl) benzene, 3,5,5-trimethyl-1-isocyanato-3-isocyanatomethyl cyclohexane, m-phenylene diisocyanate, p-phenylene diisocyanate, 2,4-tolylene diisocyanate, 2,6-tolylene diisocyanate, 4,4'-diisocyanato diphenylmethane, benzidine diisocyanate, naphthalene-1,5-diisocyanate, hexamethylene diisocyanate, tetramethylene diisocyanate, decamethylene diisocyanate, dodecamethylene diisocyanate, 4,4',4"-triphenylmethane triisocyanate, polyphenylmethylene polyisocyanates that are produced by phosgenation of aniline/formaldehyde condensation products containing up to about four aromatic rings, dianisidine diisocyanate, xylene diisocyanate, bis(2-isocyanatoethyl)fumarate, bis(2-isocyanatoethyl) cyclohex-4-ene-1,2-dicarboxylate, and bis (2-isocyanatoethyl) carbonate.

17. The composition according to claim 14, wherein said at least one polyol is chosen from diols.

18. The composition according to claim 14, wherein said at least one polyol is chosen from
(a) lactone polyols and alkylene oxide adducts thereof,
(b) polyester polyols, and alkylene oxide adducts thereof,
(c) polyoxyalkylene polyols, polyoxycycloalkylene polyols, and alkylene oxide adducts thereof, and
(d) polytetramethylene glycols.

19. The composition according to claim 14, wherein said at least one polyol has a number average molecular weight ranging from 200 to 5,000.

20. The composition according to claim 11, wherein said reactants further comprise at least one polyfunctional chain extender.

21. The composition according to claim 20, wherein said at least one polyfunctional chain extender is chosen from polyactive hydrogen compounds having a functionality of about 2 to about 4.

22. The composition according to claim 20, wherein said at least one polyfunctional chain extender is chosen from water, ethylenediamine, 1,6-diaminohexane, piperazine, tris (2-aminoethyl)amine, amine terminated polyethers, adipic acid dihydrazide, oxalic acid dihydrazide, ethylene glycol, diethylene glycol, 1,4 butane diol, 1,8 octane diol, 1,2-ethanedithiol, 1,4-butanedithiol, 2,2'-oxytris(ethane thiol), di-mercaptopropionate esters of poly(oxyethylene) diols, and tri-mercaptopropionate esters of poly(oxyethylene) triols.

23. The composition according to claim 11, wherein said reactants further comprise at least one hydrophilic component.

24. The composition according to claim 23, wherein said at least one hydrophilic component is chosen from: (i) compounds containing an ionic group, (ii) compounds containing at least one moiety capable of forming an ionic group, and (iii) compounds containing a nonionic water soluble group.

25. The composition according to claim 24, wherein said at least one hydrophilic component is a cationic compound having the following structure:

wherein
R¹ is a group chosen from $C_1$ to $C_{18}$ alkyls, $C_6$ to $C_{18}$ aryls, and $C_6$ to $C_{18}$ arylalkyls optionally substituted in and/or on the chain by at least one atom chosen from N, O, and S atoms;
R² is a group chosen from a hydrogen atom and $C_1$ to $C_{18}$ alkyls;
n is an integer ranging from about 1 to about 200; and
$X^-$ is chosen from halides, sulfates, methosulfates, ethosulfates, acetates, carbonates, and phosphates.

26. The composition according to claim 24, wherein said at least one hydrophilic component is a compound of the structure:

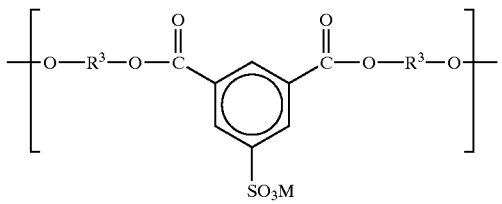

wherein M is a cation chosen from H, Na, K, Li, alkaline earth metals, and primary, secondary and tertiary ammonium cations; each R³ is independently chosen from divalent aliphatic groups having an average molecular weight ranging from about 200 to about 600 comprising at least one functional group chosen from ether and ester functional groups.

27. The composition according to claim 26, wherein said at least one functional group is chosen from:
—$CH_2CH_2$—$(OCH_2CH_2$—$)_n$—,
—$CH(CH_3)CH_2$—$(OCH(CH_3)CH_2$—$)_n$—,
—$(CH_2)_4$—$(O(CH_2)_4)_n$—, and
—$(CH_2)_mCO$—$[O(CH_2)_mCO]_n$— groups
where m is an integer ranging from about 2 to about 5 and n is an integer ranging from about 2 to about 15.

28. The composition according to claim 23, wherein said at least one hydrophilic component acts as a polyfunctional chain extender.

29. The composition according to claim 10, wherein said at least one silylated polycondensate is combined with an external surfactant.

30. The composition according to claim 11, wherein said at least one silyl containing component is chosen from:
$H_2NCH_2CH_2CH_2Si(OC_2H_5)_3$,
$HN(CH_2CH_2CH_2Si(OC_2H_5)_3)_2$,
$HSCH_2CH_2CH_2Si(OCH_3)_3$,
$HO(C_2H_4O)_3C_2H_4N(CH_3)(CH_2)_3Si(OC_4H_9)_3$,
$H_2NCH_2C_6H_4CH_2CH_2Si(OCH_3)_3$,
$HSCH_2CH_2CH_2Si(OCOCH_3)_3$,
$H_2NCH_2CH_2CH_2Si(OCH_3)_3$,

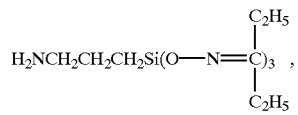

$HN(CH_3)CH_2CH_2Si(OCH_3)_3$,
$HSCH_2CH_2CH_2SiCH_3(OCH_3)_2$,
$(HOC_2H_5)_2NC_3H_6Si(OCH_3)_3$,
$H_2NCH_2CH_2CH_2NHCH_2CH_2CH_2Si(OCH_3)_3$, and
$OCNCH_2CH_2CH_2Si(OCH_3)_3$.

31. The composition according to claim 11, wherein said at least one silyl containing component acts as a polyfunctional chain extender.

32. The composition according to claim 10, wherein said at least one silylated polycondensate is in a cosmetically acceptable vehicle.

33. The composition according to claim 11, wherein said reactants further comprise at least one chain terminator component.

34. The composition according to claim 10, wherein said at least one silylated polycondensate has a Tg ranging from about −100° C. to about 15° C.

35. The composition according to claim 10, further comprising at least one additional polymer.

36. The composition according to claim 35, wherein said at least one additional polymer is chosen from anionic, cationic, amphoteric, and nonionic polymers.

37. The composition according to claim 10, further comprising at least one conventional cosmetic constituent chosen from preservatives, perfumes, active hair care agents, plasticizers, anionic, cationic, amphoteric, and nonionic surfactants, hair conditioning agents, silicone fluids, fatty esters, fatty alcohol, long chain hydrocarbons, emollients, lubricants, penetrants, lanolin compounds, protein hydrolysates, other protein derivatives, dyes, tins, bleaches, reducing agents, pH adjusting agents, sunscreens, and thickening agents.

38. A composition according to claim 10, wherein said reshapable hair styling composition is in the form of a spray, aerosol, mousse, gel, stick, mud, or lotion.

39. A reshapable hair styling composition comprising at least one siliconated polycondensate chosen from polyurethanes, polyureas, and polyurethane-ureas, wherein said composition provides a reshapable effect.

40. The composition according to claim 39, wherein said at least one siliconated polycondensate is in the form of a dispersion.

41. The composition according to claim 40, wherein said at least one siliconated polycondensate is in the form of an aqueous dispersion.

42. The composition according to claim 39, wherein said at least one siliconated polycondensate is in a cosmetically acceptable vehicle.

43. The composition according to claim 39, wherein said at least one siliconated polycondensate has a Tg ranging from about −100° C. to about 15° C.

44. The composition according to claim 39, further comprising at least one additional polymer.

45. The composition according to claim 44, wherein said at least one additional polymer is chosen from anionic, cationic, amphoteric, and nonionic polymers.

46. The composition according to claim 39, further comprising at least one conventional cosmetic constituent chosen from preservatives, perfumes, active hair care agents, plasticizers, anionic, cationic, amphoteric, and nonionic surfactants, hair conditioning agents, silicone fluids, fatty esters, fatty alcohol, long chain hydrocarbons, emollients, lubricants, penetrants, lanolin compounds, protein hydrolysates, other protein derivatives, dyes, tins, bleaches, reducing agents, pH adjusting agents, sunscreens, and thickening agents.

47. A composition according to claim 39, wherein said reshapable hair styling composition is in the form of a spray, aerosol, mousse, gel, stick, mud, or lotion.

48. A reshapable hair styling composition comprising at least one polycondensate that is functionalized with at least one group chosen from hydrolyzed silyl groups and hydrolyzable silyl groups, wherein said at least one polycondensate is the product of reactants comprising:
(a) at least one isocyanate terminated polycondensate prepolymer;

(b) at least one silyl containing component; and
wherein said composition provides a reshapable effect.

49. The composition according to claim 48, wherein said at least one polycondensate is in the form of a dispersion.

50. The composition according to claim 49, wherein said at least one polycondensate is in the form of an aqueous dispersion.

51. The composition according to claim 48, wherein said at least one isocyanate terminated polycondensate polymer is the product of reactants comprising:
(i) at least one polyisocyanate and
(ii) at least one polyol.

52. The composition according to claim 51, wherein said at least one polyisocyanate is chosen from diisocyanates.

53. The composition according to claim 51, wherein said at least one polyisocyanate is chosen from dicyclohexylmethane 4,4'-diisocyanate, 1,3-bis(isocyanatomethyl) cyclohexane, 1,3-bis(1-isocyanato-1-methylethyl) benzene, 3,5,5-trimethyl-1-isocyanato-3-isocyanatomethyl cyclohexane, m-phenylene diisocyanate, p-phenylene diisocyanate, 2,4-tolylene diisocyanate, 2,6-tolylene diisocyanate, 4,4'-diisocyanato diphenylmethane, benzidine diisocyanate, naphthalene-1,5-diisocyanate, hexamethylene diisocyanate, tetramethylene diisocyanate, decamethylene diisocyanate, dodecamethylene diisocyanate, 4,4',4"-triphenylmethane triisocyanate, polyphenylmethylene polyisocyanates that are produced by phosgenation of aniline/formaldehyde condensation products containing up to about four aromatic rings, dianisidine diisocyanate, xylene diisocyanate, bis(2-isocyanatoethyl)fumarate, bis(2-isocyanatoethyl) cyclohex-4-ene-1,2-dicarboxylate, and bis (2-isocyanatoethyl) carbonate.

54. The composition according to claim 51, wherein said at least one polyol is chosen from diols.

55. The composition according to claim 51, wherein said at least one polyol is chosen from
(a) lactone polyols and alkylene oxide adducts thereof,
(b) polyester polyols, and alkylene oxide adducts thereof,
(c) polyoxyalkylene polyols, polyoxycycloalkylene polyols, and alkylene oxide adducts thereof, and
(d) polytetramethylene glycols.

56. The composition according to claim 51, wherein said at least one polyol has a number average molecular weight ranging from 200 to 5,000.

57. The composition according to claim 48, wherein said reactants further comprise at least one polyfunctional chain extender.

58. The composition according to claim 57, wherein said at least one polyfunctional chain extender is chosen from polyactive hydrogen compounds having a functionality of about 2 to about 4.

59. The composition according to claim 57, wherein said at least one polyfunctional chain extender is chosen from water, ethylenediamine, 1,6-diaminohexane, piperazine, tris (2-aminoethyl)amine, amine terminated polyethers, adipic acid dihydrazide, oxalic acid dihydrazide, ethylene glycol, diethylene glycol, 1,4 butane diol, 1,8 octane diol, 1,2-ethanedithiol, 1,4-butanedithiol, 2,2'-oxytris(ethane thiol), di-mercaptopropionate esters of poly(oxyethylene) diols, and tri-mercaptopropionate esters of poly(oxyethylene) triols.

60. The composition according to claim 48, wherein said reactants further comprise at least one hydrophilic component.

61. The composition according to claim 60, wherein said at least one hydrophilic component is chosen from: (i) compounds containing an ionic group, (ii) compounds containing at least one moiety capable of forming an ionic group, and (iii) compounds containing a nonionic water soluble group.

62. The composition according to claim 61, wherein said at least one hydrophilic component is a cationic compound having the following structure:

$$R^1-N^+(R^2)[(CH_2CH_2O)_nH]_2X^-$$

wherein $R^1$ is a group chosen from $C_1$ to $C_{18}$ alkyls, $C_6$ to $C_{18}$ aryls, and $C_6$ to $C_{18}$ arylalkyls optionally substituted in and/or on the chain by at least one atom chosen from N, O, and S atoms;

$R^2$ is a group chosen from a hydrogen atom and $C_1$ to $C_{18}$ alkyls;

n is an integer ranging from about 1 to about 200; and $X^-$ is chosen from halides, sulfates, methosulfates, ethosulfates, acetates, carbonates, and phosphates.

63. The composition according to claim 61, wherein said at least one hydrophilic component is a compound of the structure:

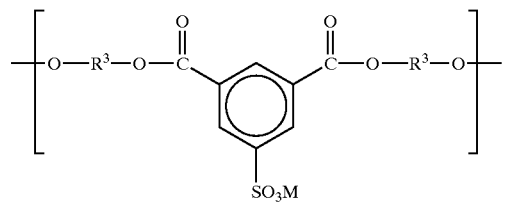

wherein M is a cation chosen from H, Na, K, Li, alkaline earth metals, and primary, secondary and tertiary ammonium cations; each $R^3$ is independently chosen from divalent aliphatic groups having an average molecular weight ranging from about 200 to about 600 comprising at least one functional group chosen from ether and ester functional groups.

64. The composition according to claim 63, wherein said at least one functional group is chosen from:

—$CH_2CH_2$—$(OCH_2CH_2$—$)_n$—,

—$CH(CH_3)CH_2$—$(OCH(CH_3)CH_2$—$)_n$—,

—$(CH_2)_4$—$(O(CH_2)_4)_n$—, and

—$(CH_2)_mCO$—$[O(CH_2)_mCO]_n$— groups where m is an integer ranging from about 2 to about 5 and n is an integer ranging from about 2 to about 15.

65. The composition according to claim 60, wherein said at least one hydrophilic component acts as a polyfunctional chain extender.

66. The composition according to claim 48, wherein said at least one polycondensate is combined with an external surfactant.

67. The composition according to claim 48, wherein said at least one silyl containing component is chosen from:

$H_2NCH_2CH_2CH_2Si(OC_2H_5)_3$, $HN(CH_2CH_2CH_2Si(OC_2H_5)_3)_2$, $HSCH_2CH_2CH_2Si(OCH_3)_3$, $HO(C_2H_4O)_3C_2H_4N(CH_3)(CH_2)_3Si(OC_4H_9)_3$, $H_2NCH_2C_6H_4CH_2CH_2Si(OCH_3)_3$,

HSCH$_2$CH$_2$CH$_2$Si(OCOCH$_3$)$_3$,
H$_2$NCH$_2$CH$_2$CH$_2$Si(OCH$_3$)$_3$,

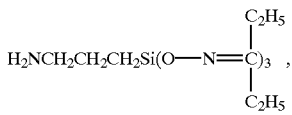

HN(CH$_3$)CH$_2$CH$_2$Si(OCH$_3$)$_3$,
HSCH$_2$CH$_2$CH$_2$SiCH$_3$(OCH$_3$)$_2$,
(HOC$_2$H$_5$)$_2$NC$_3$H$_6$Si(OCH$_3$)$_3$,
H$_2$NCH$_2$CH$_2$CH$_2$NHCH$_2$CH$_2$CH$_2$Si(OCH$_3$)$_3$, and
OCNCH$_2$CH$_2$CH$_2$Si(OCH$_3$)$_3$.

68. The composition according to claim 48, wherein said at least one silyl containing component acts as a polyfunctional chain extender.

69. The composition according to claim 48, wherein said at least one polycondensate is in a cosmetically acceptable vehicle.

70. The composition according to claim 48, wherein said reactants further comprise at least one chain terminator component.

71. The composition according to claim 48, wherein said at least one polycondensate has a Tg ranging from about −100° C. to about 15° C.

72. The composition according to claim 48, further comprising at least one additional polymer.

73. The composition according to claim 72, wherein said at least one additional polymer is chosen from anionic, cationic, amphoteric, and nonionic polymers.

74. The composition according to claim 48, further comprising at least one conventional cosmetic constituent chosen from preservatives, perfumes, active hair care agents, plasticizers, anionic, cationic, amphoteric, and nonionic surfactants, hair conditioning agents, silicone fluids, fatty esters, fatty alcohol, long chain hydrocarbons, emollients, lubricants, penetrants, lanolin compounds, protein hydrolysates, other protein derivatives, dyes, tins, bleaches, reducing agents, pH adjusting agents, sunscreens, and thickening agents.

75. A composition according to claim 48, wherein said reshapable hair styling composition is in the form of a spray, aerosol, mousse, gel, stick, mud, or lotion.

76. An aerosol device comprising a vessel, which comprises:
(1) an aerosol composition, which provides a reshapable effect and comprises a liquid phase comprising at least one composition comprising at least one silicon-containing polycondensate chosen from polyurethanes, polyureas, and polyurethane-ureas, wherein said composition provides a reshapable effect, and a propellant, and
(2) a dispenser.

77. An aerosol device comprising a vessel, which comprises:
(1) an aerosol composition, which provides a reshapable effect and comprises a liquid phase comprising at least one composition comprising at least one silylated polycondensate chosen from polyurethanes, polyureas, and polyurethane-ureas, wherein said composition provides a reshapable effect, and a propellant, and
(2) a dispenser.

78. An aerosol device comprising a vessel, which comprises:
(1) an aerosol composition, which provides a reshapable effect and comprises a liquid phase comprising at least one composition comprising at least one siliconated polycondensate chosen from polyurethanes, polyureas, and polyurethane-ureas, wherein said composition provides a reshapable effect, and a propellant, and
(2) a dispenser.

79. An aerosol device comprising a vessel, which comprises:
(1) an aerosol composition, which provides a reshapable effect and comprises a liquid phase comprising at least one composition comprising at least one polycondensate that is functionalized with at least one group chosen from hydrolyzed silyl groups and hydrolyzable silyl groups, wherein said at least one polycondensate is the product of reactants comprising:
(a) at least one isocyanate terminated polyurethane-urea prepolymer; and
(b) at least one silyl containing component, wherein said composition provides a reshapable effect,
and a propellant, and
(2) a dispenser.

80. A method of cosmetically treating hair, comprising applying to the hair before, during, or after shaping of a hairstyle of said hair a composition comprising at least one silicon-containing polycondensate chosen from polyurethanes, polyureas, and polyurethane-ureas, wherein said composition provides a reshapable effect.

81. A method of cosmetically treating hair, comprising applying to the hair before, during, or after shaping of a hairstyle of said hair a composition comprising at least one silylated polycondensate chosen from polyurethanes, polyureas, and polyurethane-ureas, wherein said composition provides a reshapable effect.

82. A method of cosmetically treating hair, comprising applying to the hair before, during, or after shaping of a hairstyle of said hair a composition comprising at least one siliconated polycondensate chosen from polyurethanes, polyureas, and polyurethane-ureas, wherein said composition provides a reshapable effect.

83. A method of cosmetically treating hair, comprising applying to the hair before, during, or after shaping of a hairstyle of said hair a composition comprising at least one polycondensate that is functionalized with at least one group chosen from hydrolyzed silyl groups and hydrolyzable silyl groups, wherein said at least one polycondensate is the product of reactants comprising:
(a) at least one isocyanate terminated polyurethane-urea prepolymer; and
(b) at least one silyl containing component, wherein said composition provides a reshapable effect.

84. A method of reshaping hair, comprising:
(1) applying to the hair before, during, or after the initial shaping of the hairstyle, a composition comprising at least one silicon-containing polycondensate chosen from polyurethanes, polyureas, and polyurethane-ureas, wherein said composition provides a reshapable effect, and
(2) thereafter reshaping the hairstyle at least once, wherein no additional composition or heat is added.

85. A method of reshaping hair, comprising:
(1) applying to the hair before, during, or after the initial shaping of the hairstyle, a composition comprising at least one silylated polycondensate chosen from polyurethanes, polyureas, and polyurethane-ureas, wherein said composition provides a reshapable effect, and (2) thereafter reshaping the hairstyle at least once, wherein no additional composition or heat is added.

86. A method of reshaping hair, comprising:
(1) applying to the hair before, during, or after the initial shaping of the hairstyle, a composition comprising at least one siliconated polycondensate chosen from polyurethanes, polyureas, and polyurethane-ureas, wherein said composition provides a reshapable effect, and
(2) thereafter reshaping the hairstyle at least once, wherein no additional composition or heat is added.

87. A method of reshaping hair, comprising:
(1) applying to the hair before, during, or after the initial shaping of the hairstyle, a composition comprising at least one polycondensate that is functionalized with at least one group chosen from hydrolyzed silyl groups and hydrolyzable silyl groups, wherein said at least one polycondensate is the product of reactants comprising:
  (a) at least one isocyanate terminated polyurethane-urea prepolymer; and
  (b) at least one silyl containing component, wherein said composition provides a reshapable effect, and
(2) thereafter reshaping the hairstyle at least once, wherein no additional composition or heat is added.

* * * * *

UNITED STATES PATENT AND TRADEMARK OFFICE
CERTIFICATE OF CORRECTION

PATENT NO.    : 6,520,186 B2
DATED         : February 18, 2003
INVENTOR(S)   : Isabelle Rollat et al.

It is certified that error appears in the above-identified patent and that said Letters Patent is hereby corrected as shown below:

Column 8,
Lines 30-34,

"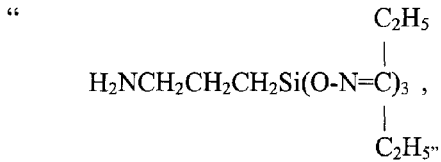"

should read

--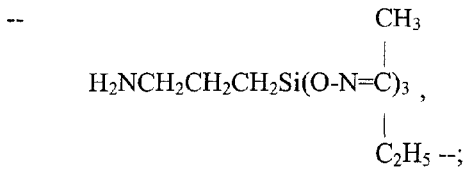--;

Column 18,
Line 1, after "claim 14,", delete "wherein,";

Column 19,
Lines 55-59,

"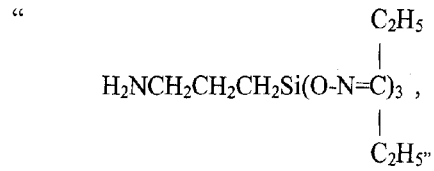"

should read

--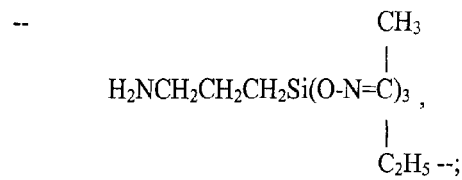--;

Column 20,
Line 67, after "prepolymer,", insert -- and --;

UNITED STATES PATENT AND TRADEMARK OFFICE
CERTIFICATE OF CORRECTION

PATENT NO. : 6,520,186 B2
DATED : February 18, 2003
INVENTOR(S) : Isabelle Rollat et al.

It is certified that error appears in the above-identified patent and that said Letters Patent is hereby corrected as shown below:

<u>Column 23,</u>
Lines 4-8,

"
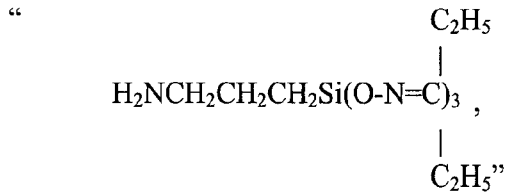
, should read

--
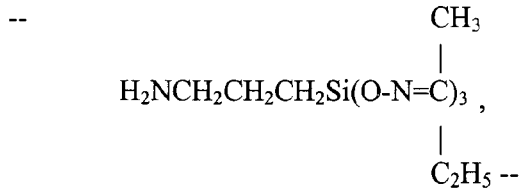
,

--

Signed and Sealed this

Fifteenth Day of July, 2003

JAMES E. ROGAN
*Director of the United States Patent and Trademark Office*